US007119902B2

(12) United States Patent
Beaumont

(10) Patent No.: US 7,119,902 B2
(45) Date of Patent: Oct. 10, 2006

(54) CALIBRATION FOR OPTICAL FILTER

(75) Inventor: Matt Beaumont, Ipslach (GB)

(73) Assignee: Production Resource Group, L.L.C., New Windsor, NY (US)

(*) Notice: Subject to any disclaimer, the term of this patent is extended or adjusted under 35 U.S.C. 154(b) by 0 days.

(21) Appl. No.: 11/215,992

(22) Filed: Aug. 30, 2005

(65) Prior Publication Data
US 2006/0077389 A1 Apr. 13, 2006

Related U.S. Application Data

(60) Division of application No. 10/763,293, filed on Jan. 23, 2004, now Pat. No. 6,937,338, which is a continuation of application No. 10/243,165, filed on Sep. 11, 2002, now abandoned, which is a division of application No. 09/778,242, filed on Feb. 6, 2001.

(60) Provisional application No. 60/181,525, filed on Feb. 10, 2000.

(51) Int. Cl.
G01N 21/25 (2006.01)

(52) U.S. Cl. .................. 356/419; 356/418; 356/416

(58) Field of Classification Search ................. None
See application file for complete search history.

(56) References Cited

U.S. PATENT DOCUMENTS

| 3,818,198 A | 6/1974 | Walker et al. ............... 356/233 |
|---|---|---|
| 4,093,991 A | 6/1978 | Christie et al. ............. 356/319 |
| 4,602,160 A | 7/1986 | Mactaggart ............... 250/341.5 |
| 5,282,121 A | 1/1994 | Bornhorst et al. .......... 362/294 |
| 5,515,119 A | 5/1996 | Murdock et al. ........... 352/131 |
| 5,528,431 A | 6/1996 | Wilkins ...................... 359/885 |
| 5,729,347 A | 3/1998 | So .............................. 356/416 |
| 5,852,498 A | 12/1998 | Youvan et al. .............. 356/417 |
| 6,157,025 A | 12/2000 | Katagiri et al. ............. 250/226 |
| 6,359,724 B1 | 3/2002 | Katagiri et al. ............. 359/333 |
| 6,937,338 B1 | 8/2005 | Beaumont ................... 356/419 |
| 2001/0038452 A1 | 11/2001 | Beaumont ................... 356/416 |
| 2003/0020909 A1* | 1/2003 | Adams et al. ............... 356/326 |
| 2003/0071999 A1 | 4/2003 | Beaumont ................... 356/416 |
| 2004/0150825 A1 | 8/2004 | Beaumont ................... 356/416 |

OTHER PUBLICATIONS

'Color', http://en.wikipedia.org/wiki/Color.

* cited by examiner

Primary Examiner—Thong Nguyen
Assistant Examiner—Arnel C. Lavarias
(74) Attorney, Agent, or Firm—Fish & Richardson P.C.

(57) ABSTRACT

Calibrating each of a plurality of driven optical filters. The color parameters of the driven optical filters are characterized for the individual optical filter. These color parameters are used as calibration data to calibrate more standard information.

11 Claims, 3 Drawing Sheets

CALIBRATION FOR OPTICAL FILTER

CROSS-REFERENCE TO RELATED APPLICATIONS

This application is a divisional of U.S. application Ser. No. 10/763,293, filed Jan. 23, 2004; now U.S. Pat. No. 6,937,338 which is a continuation of U.S. application Ser. No. 10/243,165, filed Sep. 11, 2002 now abandoned; which is a divisional of U.S. application Ser. No. 09/778,242, filed Feb. 6, 2001; which claims the benefit of U.S. provisional application Ser. No. 60/181,525, filed Feb. 10, 2000.

BACKGROUND

Different kinds of optical filters are known. Optical filters can be formed by coating a blank to form an optical filter which has different characteristics in different locations of the filter.

Examples of such filters are found in U.S. Pat. No. 5,426,576. In these optical filters, the amount of color saturation may vary based on the distance along a gradient axis. The gradient axis can be a linear gradient axis, or a circumferential gradient axis, in this patent. Also, two filters can be used together to form a cross fader.

Different kinds of coated optical filters are also known. In general, these coated optical filters may have characteristics that vary based on the amount of the coating.

SUMMARY

The present application teaches a system which enables consistent color from each of a plurality of luminaires, each of which use a coated optical filter.

According to the present application, a special technique of calibration is described for an optical filter which has characteristics that vary based on a parameter of the optical filter, e.g. color that changes along a gradient axis.

BRIEF DESCRIPTION OF THE DRAWINGS

These and other aspects will now be described in detail, with reference to the accompanying drawings, wherein.

DETAILED DESCRIPTION

Figure 1:
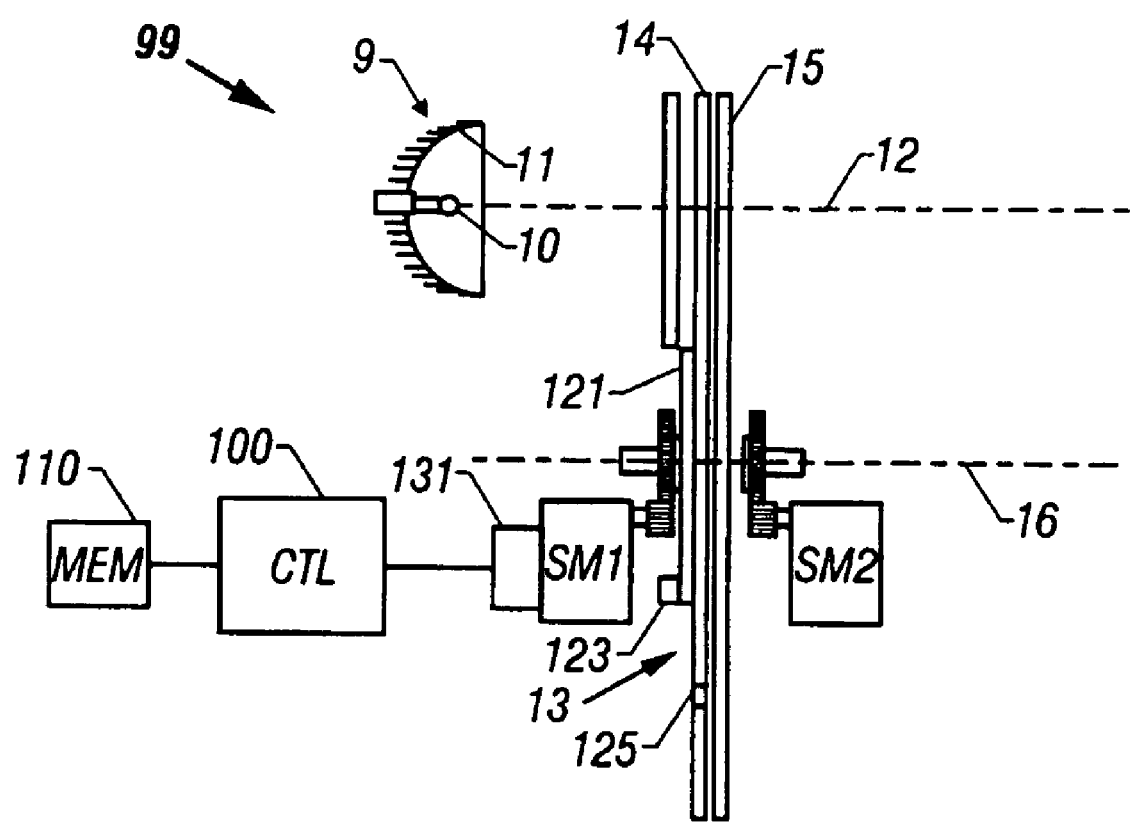
FIG. 1 shows a block diagram of the luminaire system.

FIG. 1 shows a system in which a light transmission device 99 including a lamp assembly 9, having lamp 10 and reflector 11 is caused to transmit light along an optical axis 12. A color filter assembly 13 is formed of two color filters 14 and 15 placed along the optical axis and rotatable about axis 16. Each of the color filters, such as 14, may include an alignment mark 125. The alignment mark 125 may include, for example, a physical hole in the filter. The alignment mark allows the system to determine a set point in the filter, for example the beginning of a certain color spectrum. The filters are coated with a varying amount of filtering medium, so that different areas on the filter produce a different color effect.

The two color filters can be moved relative to one another by the motors SM1 and SM2. By moving the color filters, the degree of saturation changes, and hence the color output changes. The motors SM1 and SM2 are controlled by a controller 100. The controller 100 operates according to a prestored program which may be stored in its memory 110.

According to the present system, each luminaire 99 should, on cue, produce the same color. This is done according to the present system by calibrating each of the filters 14, 15 in each luminaire 99 based on a reference standard. The calibration allows each luminaire to know an exact position of the filter that produces a specific color effect even if there are positional and/or color differences between the filters.

The system used herein may use a parametric color filter of the type described in U.S. Pat. No. 5,426,576. Alternatively, any other kind of filter that has characteristics that vary according to a parameter of the filter, here a distance along a gradient axis, may be compensated using this system.

No two filters, in general, will be exactly the same. One technique used herein is to provide tight tolerances on certain aspects of the filter, and allow other aspects of the filter to be corrected by the calibration process. For example, spectral form, radiality, start and end points may be tightly controlled. Other parameters such as relationship of the aperture hole to the coating edge, and linearity, may be more loosely controlled.

In addition to manufacturing differences in the filter itself, another source of errors in the filters may involve the combining of the filters 14, 15 with the hub that carries the filters shown as 121. In this embodiment, the hub includes a magnet 123 which is used to set a 'home' position of the filter relative to the optical axis 12 of the luminaire 99. In assembling the filters, a jig may align the center of the magnet 123 to the aperture hole in the filter. Errors in this assembly may arise, for example due to the physics of the way the manufacturing jig mounts the devices. The jig can not have too tight a fit in the aperture hole, because of the fragile nature of certain filters. For example, certain filters may be manufactured from Vycor (™); a form of fused silica manufactured by Corning, Inc. Other sources of manufacture and assembly errors may be also be expected. In general, this may provide an error up to plus or minus 0.5 degrees.

Figure 2:
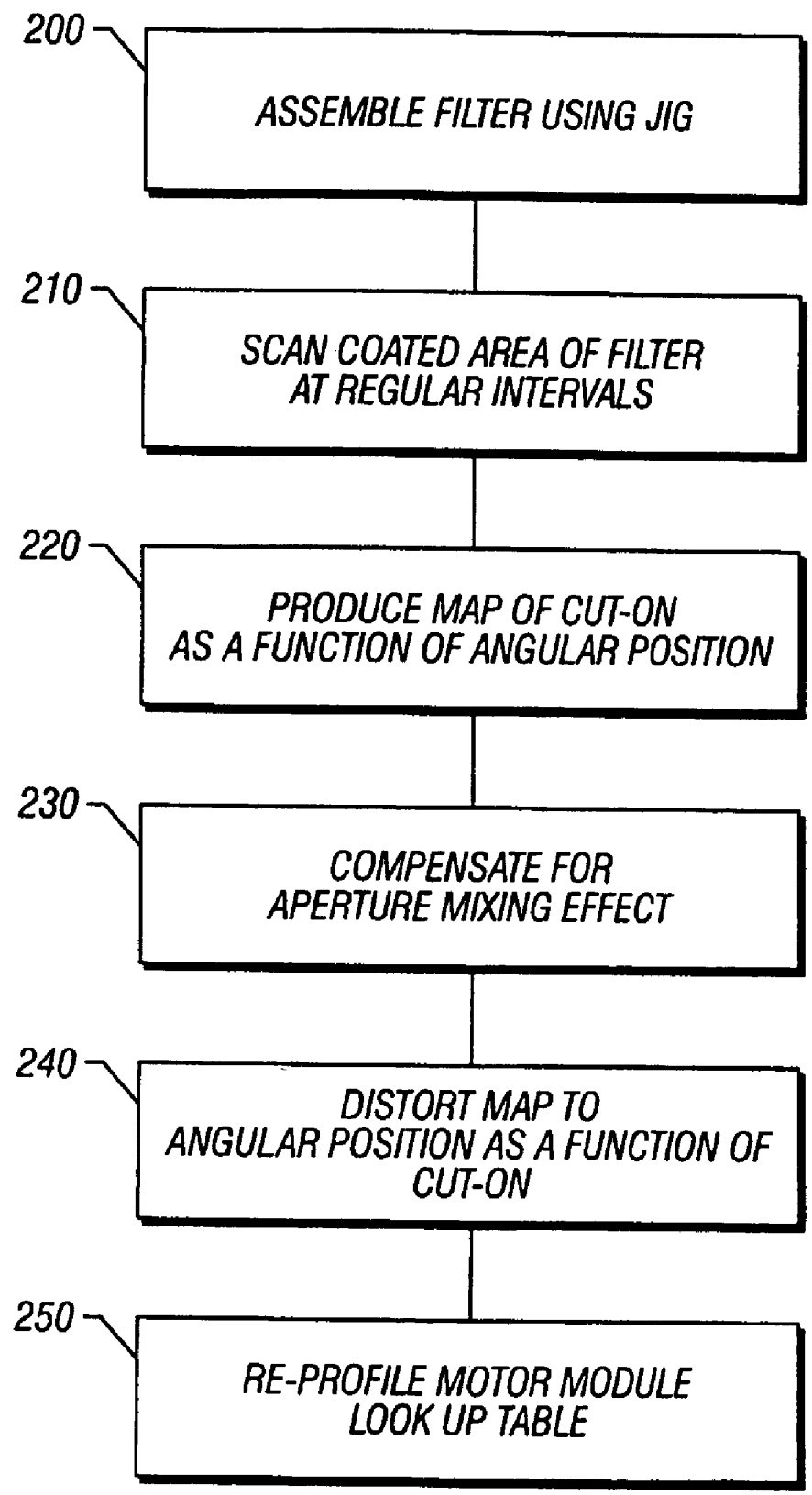
FIG. 2 shows a flow diagram of forming the filters.

The calibration operation is shown in FIG. 2. This calibration operation may be carried out on a test jig for example. At 200, the parametric color filter is assembled using the jig. As described above, this is done using the best possible accuracy, although it should be understood that certain errors will inevitably occur.

In order to calibrate each filter, the filters must first be characterized. 210 shows scanning the coated area of the filter at intervals. The scanning can use an ultraviolet or visible spectrophotometer to scan the filter at regular intervals. The intervals between scans should remain constant for each filter so that the characteristics of each filter are consistent from filter to filter. Each scan produces a set of data in the form of transmittance as a function of wavelength. The scan is then analyzed to find the location where the value cuts on to 50 percent. The color at any point in the filter can then be represented as a single value.

This creates a map of points showing the optical characteristics of the filter as a function of the position on the filter. The maps can use a specified point in the slope curve of the data. Here, that specified point is selected to be 50 percent of the cut on value. Other slope points could also be selected. The map essentially becomes a table of 50 percent cut on points and a position where those 50 percent cut on points occur. This may be stored, for example, as a 16-bit encoder count.

This produces a map at 220 indicating the position of cut on as a function of angular position. Each map is unique to each filter.

The spectrophotometer which is used may have a maximum aperture of scanning that may be of a different size, usually smaller than, the scanning beam used for the final illumination. For example, the spectrophotometer may have an aperture of 5 mm, while the light beam may scan at 30 mm. Therefore, any individual scan may not be representative of the color that would be produced when the filter is used in a lighting fixture which has a much larger aperture, e.g. 30 mm. At 230, the map is compensated for the aperture mixing affect, essentially compensating for the larger aperture. The correction may be done by calculating an approximate weighted mean cut on for each of a plurality of smaller points in the map. Ideally, angular distances between scans of the filter will be an even fraction of the angle that the aperture occupies.

Figure 3:
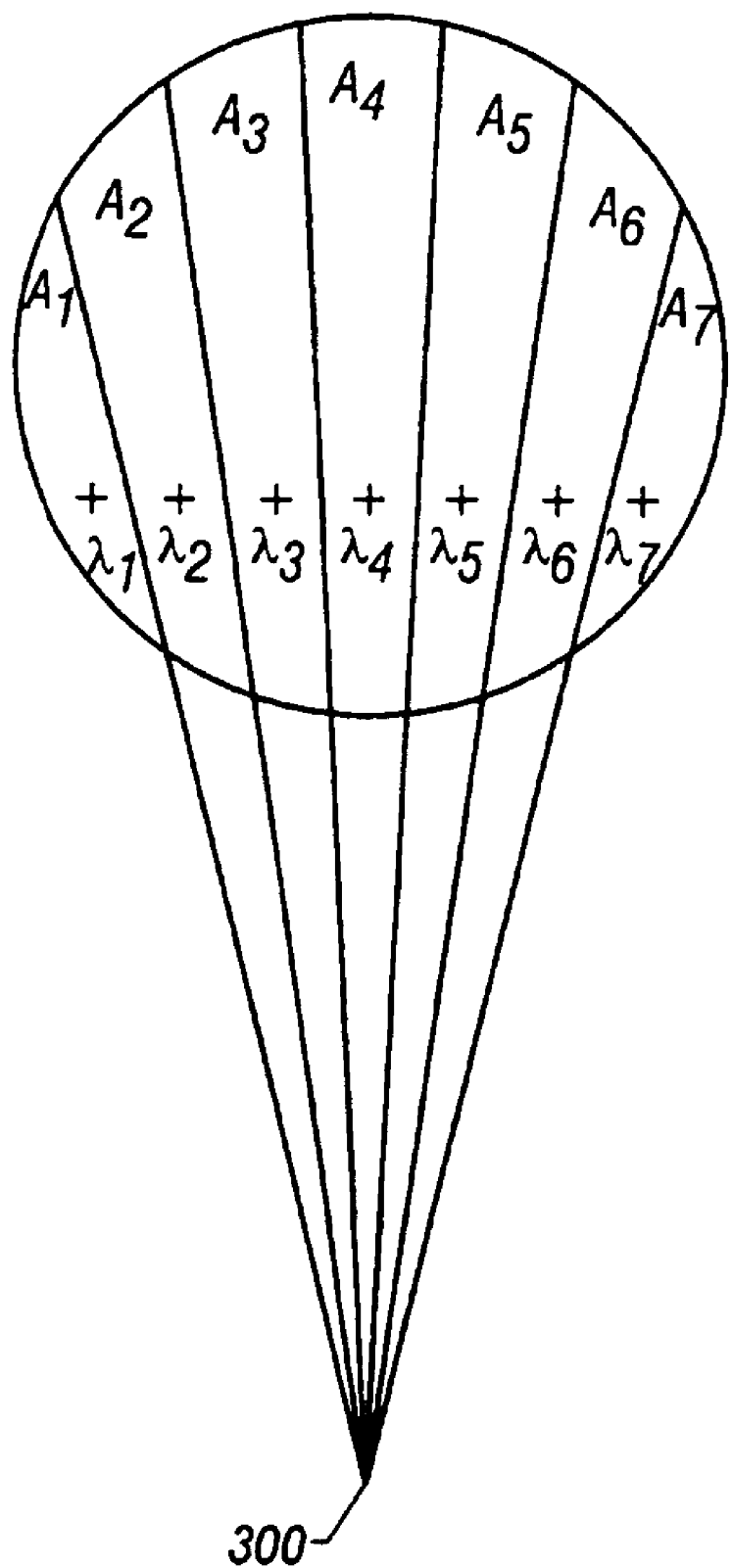
FIG. 3 shows a diagram of rotation compensation for the filter characterization.

An area occupied by each scan in the aperture is first calculated. In the system used according to the preferred mode, the coating is radially measured. The aperture can be divided into radially divided segments centered on the center of rotation as shown in FIG. 3. The center of rotation 300 is used as a common point. A plurality of segments are formed. Each segment has an area A1, A2 ... An, and a corresponding measured wavelength λ1, or segment a1 and the like.

Once the area of each of the segments has been determined, the proportion that each segment occupies as compared with the total aperture area is next calculated.

$$\pi r^2 = \sum (A_1 \rightarrow A_7)$$

$$\text{Relative area}(a) = \frac{\text{segmented area}(A)}{\pi r^2}$$

The diagram of FIG. 3 shows seven segments. Within each segment, there is a specified 50 percent cut on represented by λ. The weighted means of the segments is therefore $$Wm = (a_1\lambda_1) + (a_2\lambda_2) + (a_3\lambda_3) + (a_4\lambda_4) + (a_5\lambda_5) + (a_6\lambda_6) + (a_7\lambda_7) \text{ or}$$

$$Wm = \sum_{i=1}^{7} (a_i\lambda_1)$$

This calculation may be repeated for each practical point on the map. That is, each aperture point may be characterized fully within the coated region of the filter.

By using this technique, most of the filter can be calibrated. The maximum calibrated region of the filter may be 360 degrees minus the angle occupied by the clear region in the angle occupied by one whole aperture. For example, for a 30 degree aperture and a 60 degree clear region, 270 degrees of the filter may be calibrated.

Once this has been completed, at 250, the map or look up table is distorted to show angular position as a function of cut on. This may be done by interpolation. A set of target values for each filter is determined. These may be, for example, ideal 50 percent cut on values. These target values may be evenly spaced within the 50 percent of the cut on range of the filter's characteristic. Alternatively, they may be tailored in order to increase resolution in certain areas of the filter. While both of these techniques will work, it may be essential that the same target values be used for every like filter, in order to make sure that the calibrated values look the same from each luminaire. The number of target values may be set to less than the number of values in the motor profiling table for a specified region.

The positions for these target values are then found by interpolation of the data in the distorted map. These positions are used for the calibration process. At 250, the motor module lookup table is re-profiled using this calibration data. Each motor, such as SM1, has an associated lookup table 131 along with servo motor drive electronics. The lookup table may include a specified number of positions, each position corresponding to a color. For example, there may be 49 positions. These 49 positions represent the start and end points of 48 line segments. These form a linear approximation to occur from which the motor moves are profiled in the 270 degree calibrated region of the filter. The profile contains 49, 16-bit positions which extend from 8192 to 57344, and are linearly spaced at one K intervals. The motor profiling operation may move the motor to precise locations by interpolation between points on the table.

The positions of the target values may also be in the range of 8192–57344. These positions replace the linearly-spaced positions in the motor profiling table. This hence profiles the motor according to the filter map of weighted mean 50 percent cut on values.

Using this technique allows several fixtures to be sent the same color data by a controlling console. Each filter is moved to its unique position and outputs the same color.

Although only a few embodiments have been disclosed in detail above, other modifications are possible. For example, the system above has described one specific filter. It should be understood that other filters, including filters on which the gradient axis is linear or two-dimensional could similarly be characterized. The techniques given above of characterizing the radial filter can be extended to linear filters, and in many ways might be more simple in linear filters.

In addition, while this system has described distorting a lookup table in the servo drive electronics, other ways of using this calibration data should also be understood. For example, the calibration data could be stored as the correction factor for use with existing electronics.

All such modifications are intended to be encompassed within the following claims, in which:

What is claimed is:

1. A method, comprising:
   forming an optical filter having an optical characteristic that varies according to a parameter thereof;
   using an optical device to form information about said optical characteristic on the optical filter, and to obtain information which is individual for each specific optical filter, said optical device having a first aperture; and
   determining a second aperture of a light beam which will be used to illuminate the optical filter;
   determining differences between said first and second apertures;
   using said information which is individual for each specific optical filter and information about said differences to modify a profile used to move said optical filter.

2. A method as in claim 1, wherein said profile used to move said optical filter is a profile that drives a motor.

3. A method as in claim 1, wherein said using an optical device comprises using a spectrophotometer to scan a region of the filter to form a set of data indicating transmittances as a function of wavelength.

4. A method as in claim 3, further comprising analyzing said data to find a specified point in a slope curve formed by said data, said specified point forming said information which is individual to each specific optical filter.

5. A method as in claim 4, wherein said specified point in said slope curve is at 50 percent of the cut on point.

6. A method as in claim 4, wherein said specified point in said slope curve is a value that allows any color at any point in the filter to be represented by a single value.

7. A method as in claim 1, wherein said information about said differences includes information compensating for an aperture mixing effect caused by said different aperture.

8. A method as in claim 7, wherein said compensating comprises determining values at different scans in the first aperture, and averaging said values over said second aperture.

9. A method as in claim 8, wherein said optical filter assembly is substantially round, and said determining values comprises determining radial segment values.

10. A method as in claim 8, wherein said determining values comprises determining a first area of the segment encompassed by said first aperture, and determining a proportion of said first area within the second area represented by an area of said second aperture.

11. A method as in claim 8, wherein said compensating comprises determining an area of the first aperture and an area of the second aperture, and a ratio between said areas, and weighting a value of said first aperture according to said ratio.

* * * * *